United States Patent [19]

Chen

[11] Patent Number: 4,702,393
[45] Date of Patent: Oct. 27, 1987

[54] COMPENSATING DILUTER/DISPENSER

[75] Inventor: Bu S. Chen, Miami, Fla.

[73] Assignee: Hyperion, Inc., Miami, Fla.

[21] Appl. No.: 698,938

[22] Filed: Feb. 7, 1985

[51] Int. Cl.⁴ .............................................. B67D 5/30
[52] U.S. Cl. ....................................... 222/1; 222/14;
222/283; 222/309; 277/165; 364/571; 436/179
[58] Field of Search ................. 222/63, 282, 283, 309,
222/14-22, 1; 364/571, 509, 465; 277/165;
73/14; 422/100; 436/179, 180

[56] References Cited

U.S. PATENT DOCUMENTS

| | | | |
|---|---|---|---|
| 3,418,001 | 12/1968 | Rentschler et al. | 277/165 |
| 3,655,094 | 4/1972 | Hobbs . | |
| 3,798,431 | 3/1974 | Schulkind et al. | 364/571 |
| 3,869,068 | 3/1975 | Chen . | |
| 3,915,651 | 10/1975 | Nishi | 422/100 X |
| 3,982,667 | 9/1976 | Chen . | |
| 4,244,919 | 1/1981 | Chen . | |
| 4,331,262 | 5/1982 | Snyder et al. | 222/63 X |
| 4,340,153 | 7/1982 | Spivey | 222/1 |
| 4,475,666 | 10/1984 | Bilbrey et al. | 222/14 |
| 4,487,333 | 12/1984 | Pounder et al. | 222/129.4 X |
| 4,566,703 | 1/1986 | Zitting | 277/165 |
| 4,577,874 | 3/1986 | Zitting | 277/165 |
| 4,586,546 | 5/1986 | Mezei et al. | 436/180 X |

Primary Examiner—Robert J. Spar
Assistant Examiner—P. McCoy Smith
Attorney, Agent, or Firm—Lockwood, Alex, Fitzgibbon & Cummings

[57] ABSTRACT

An improved precision diluter/dispenser device is provided with features for effecting automatic compensation for non-linearity of aspirated fluid volumes of the particular piston and cylinder syringe assemblies that are included with the diluter/dispenser device in order to enhance the accuracy of the device by varying the piston stroke length in order to correct for non-linearity of aspirated or dispensed fluid volumes. Suitable correction factors are programmed into the control mechanism of the device in order to automatically make the necessary adjustments in stroke length so as to significantly enhance the linearity of the movement of fluid volumes throughout the working volume of the piston and cylinder assembly, whether the movement of fluid be of a very small percentage or a very large percentage of the volume capacity of the assembly. Additionally, an improved seal assembly is provided within a precision diluter/dispenser device in order to enhance the accuracy and precision life of the device and to reduce service requirements.

11 Claims, 7 Drawing Figures

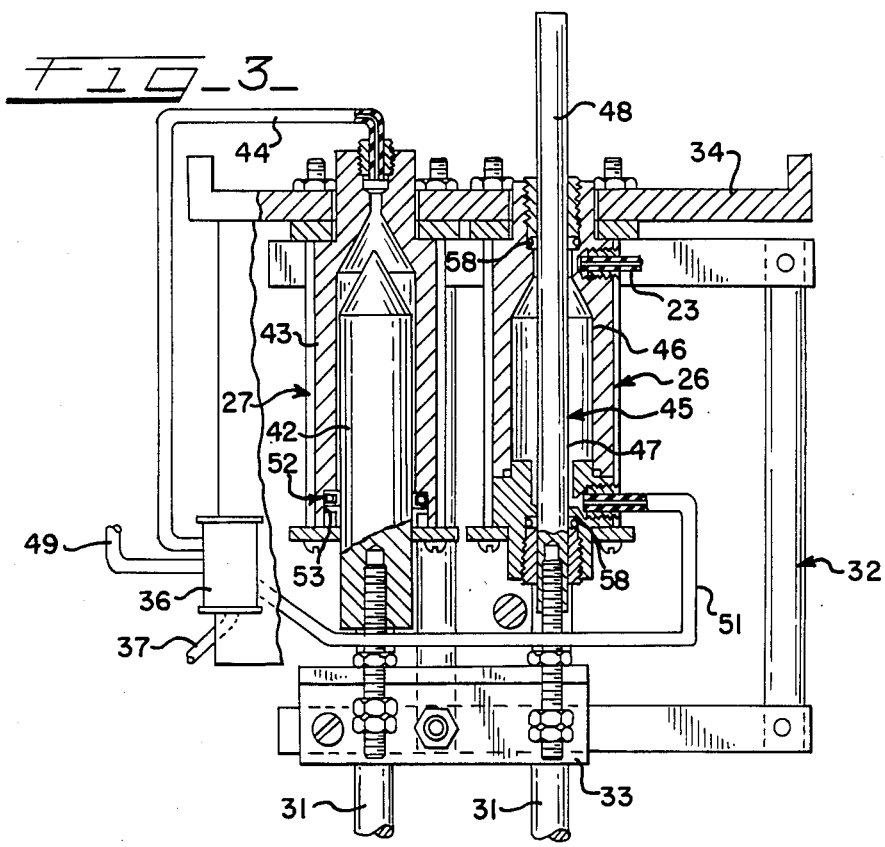
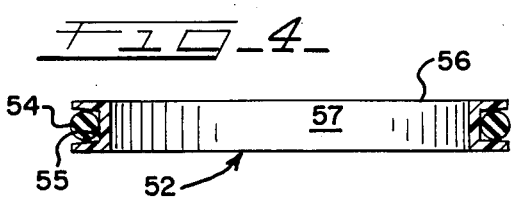
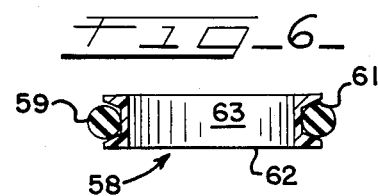
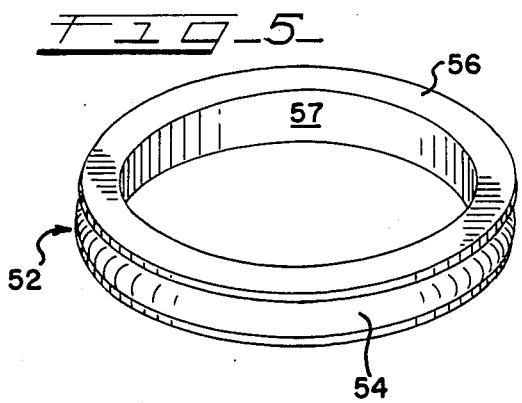
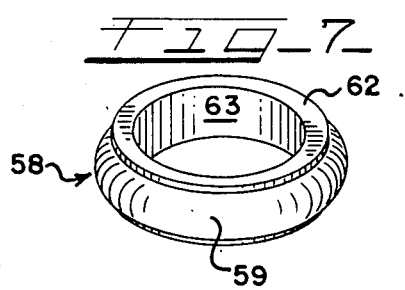

COMPENSATING DILUTER/DISPENSER

DESCRIPTION

BACKGROUND AND DESCRIPTION OF THE INVENTION

The present invention generally relates to the automatic dilution or dispensing of fluids, more particularly to an apparatus and a method for diluting or dispensing fluids in a manner that includes automatic compensation for the non-linearity of aspirated fluid volumes including non-linearity due to unavoidable variations in cross-sectional area throughout the length of precision ground pistons of the aspirating syringe assemblies of diluter/dispenser devices or variations in cylinder bores of classical syringe designs which employ a plunger drive against the cylinder internal diameter. In connection with the compensating diluting or dispensing apparatus and method according to this invention, each piston and cylinder, or syringe, assembly is controlled by a drive assembly that compensates for deviations from the ideal, linear aspiration volume scheme for a syringe assembly of that size. The drive assembly follows an appropriate program of compensation factors for selectively adjusting the extent of movement of the piston of that particular syringe assembly in order to provide volume displacements that exhibit substantially enhanced conformity with the ideal, linear volume displacement scheme expected of the particular syringe, limited only by its inherent precision.

Laboratory test devices for performing qualitative or quantitative analyses of fluids, such as blood cell counts or hemoglobin determination on blood samples, typically require substantial dilution of the sample fluids in order to minimize the size of sample needed or in order to satisfy the requirements of laboratory procedures such as those involving colorimetric analysis. Automatic diluters, which may be free standing or a component of a more comprehensive instrument, are known and available for carrying out automatic dilution or automatic dispensing of diluents or reagents.

An extremely important consideration and objective of the various currently available automatic diluters is that a diluter must be as accurate and precise as possible so as to minimize deviation between a volume of fluid that is actually aspirated or dispensed when compared with the volume that the automatic diluter indicates has been aspirated or dispensed. A minute deviation between the actual volume and the expected volume (the volume that the device indicates has been aspirated or dispensed) typically will seriously decrease the reliability of the particular laboratory analysis being performed. Previously known automatic diluter/dispenser devices have been reasonably successful in providing for the movement of fluids in an accurate and precise manner. One such important advance in this regard is described in U.S. Pat. No. 3,655,094, incorporated by reference hereinto, which includes the use of precision piston and cylinder, or syringe, assemblies. This device is illustrative of automatic diluters that include means to ensure piston movement that is especially responsive so as to all but entirely eliminate inaccuracies that are caused by imprecise movement of each piston and of its drive components such as stepper motors, gears and drive spindles.

Even though great strides have been made in improving the accuracy and precision of automatic diluter/dispenser devices, inaccuracies throughout their operating ranges (variable versus fixed volume) still present a problem. Although the syringe assemblies incorporated into these devices are precision manufactured in order to meet extremely tight tolerances, the fact remains that known manufacturing techniques are incapable of removing all non-uniformities. The cross-sectional area of a precision manufactured piston will vary somewhat throughout the length of the piston or the length of the cylinder bore, which variations will cause non-linearity of volumes aspirated or dispensed with a syringe assembly incorporating such a piston. Inaccuracies of this type are especially critical when the volume of fluid being aspirated or dispensed is a small percentage of the total volume of the particular syringe. Further inaccuracies can develop due to very minute changes in the location or configuration of seals within piston and cylinder or syringe assemblies which tend to develop during normal operation after extensive use. Another disadvantage which can become evident upon extended use is the need to lubricate these syringe seals to prevent sticking and undesirable noise.

The present invention recognizes these problems and substantially eliminates their detrimental effects. An improved piston stroke regulating assembly is provided which includes a microprocessor controlled drive assembly that automatically compensates for the non-linearity of aspirated volumes that is exhibited by the particular syringe when it is used without compensating for its non-linearity. Corrections are automatically made so that the stroke length needed to aspirate a particular volume of fluid is increased or decreased by an amount such that the volume actually aspirated at virtually any location along the piston is substantially identical to the rated or expected volume at that location along the piston. Without this modified stroke regulating assembly, the non-linearity of the piston and cylinder or syringe assembly will result in piston movement that may be too great at one volume or volumes, while being too little at another volume or volumes. Modification schemes are developed in this regard by comparing actual volumes aspirated by a particular syringe assembly with expected volumes at a plurality of aspirating locations in order to develop a set of modification factors that are used to make the necessary adjustments to the microprocessor control assembly that will control its movement when it is used to aspirate and dispense fluids. Additionally, each piston and cylinder or syringe assembly is preferably provided with a seal assembly for the movement interface between the piston and the cylinder, which seal assembly provides a preferably lubricious sealing surface that is substantially rigid and stationary and that cylindrically overlies the surface of the piston.

It is accordingly a general object of the present invention to provide an improved automatic diluter/dispenser device and method.

Another object of the present invention is to provide a precision diluter/dispenser apparatus and method which includes a syringe stroke regulating assembly that corrects for the non-linearity of aspirated volumes that is experienced by the particular syringe piston and cylinder assembly in order to, in effect, remove bias error, thereby assuring that volumetric accuracy approximates the inherent precision of the machine and calibration system.

Another object of this invention is to provide an improved diluter/dispenser apparatus having enhanced long-life seal assemblies that avoid distortion which can lead to inaccurate aspiration.

These and other objects, features and advantages of this invention will be more clearly appreciated and understood through a consideration of the following detailed description.

BRIEF DESCRIPTION OF THE DRAWING

In the course of this description, reference will be made to the attached drawings, wherein:

FIG. 3 is a rear end view, partially broken away and partially in section, showing preferred structural details of the apparatus;

FIG. 4 is an enlarged detail, sectional view of the diluent piston and cylinder seal assembly shown in FIG. 3;

FIG. 5 is a perspective view of the seal assembly shown in FIG. 4;

FIG. 6 is an enlarged detail, sectional view of the seal assemblies included in the sample piston and cylinder assembly of FIG. 3; and FIG. 7 is a perspective view of the seal assembly shown in FIG. 6.

DESCRIPTION OF THE PARTICULAR EMBODIMENTS

Figure 1:
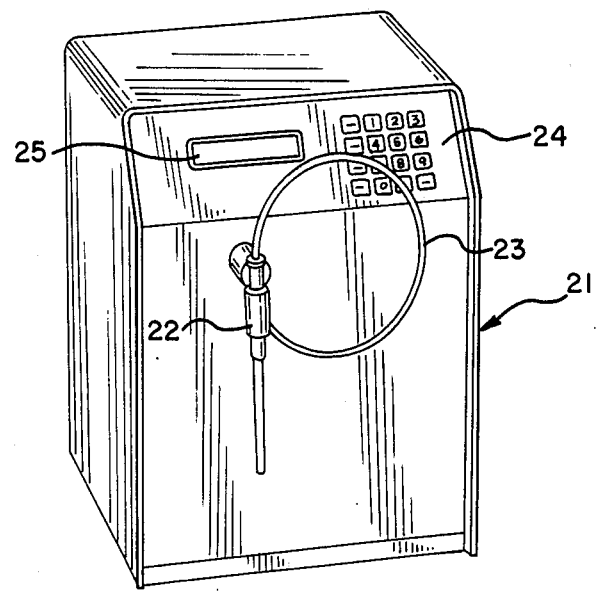
FIG. 1 is a generally front perspective view of an automatic diluter/dispenser apparatus according to this invention.

A diluter apparatus within which the present invention can be embodied and which is generally designated as 21 in FIG. 1 includes a detachable probe 22 and its tubing 23 which connects the probe 22 with the rest of the apparatus 21. Detachable probe 21 is readily inserted into appropriate containers such as test tubes or beakers for aspirating and storing samples to be analyzed and for dispensing the stored sample and measured volume of diluent from the probe 22. A suitable key pad 24 may be included to permit the operator to conveniently provide selected input to the microprocessor of the apparatus 21, and a display 25 is preferably provided to confirm inputted data and to display messages such as the operating mode of the apparatus.

Figure 2:
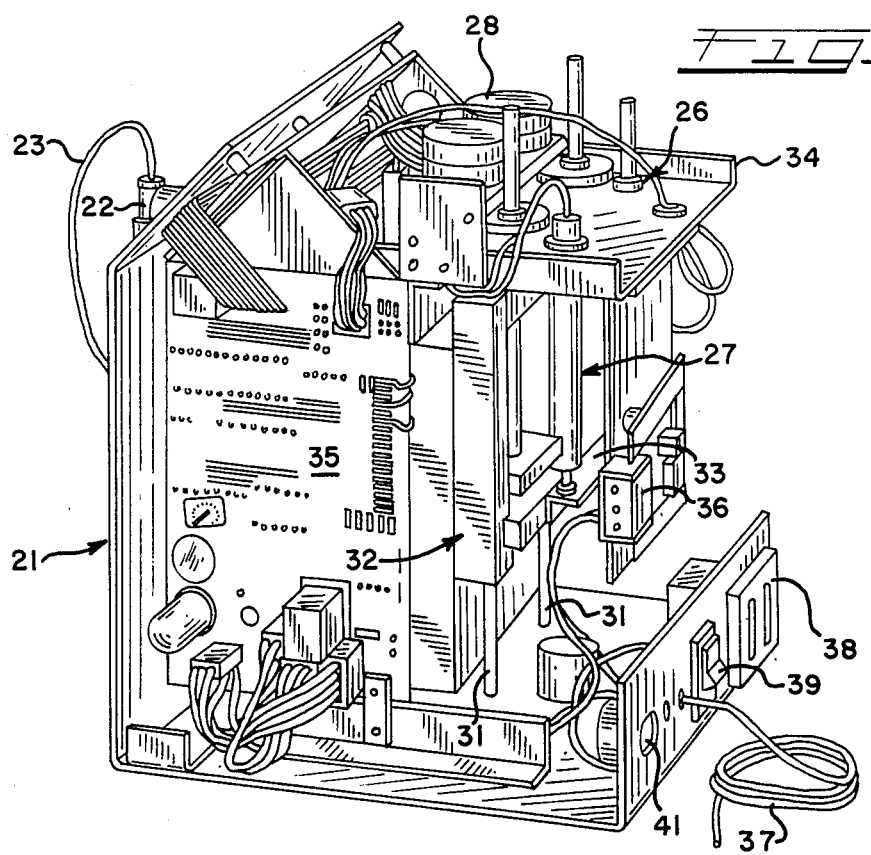
FIG. 2 is a generally rear perspective view of the apparatus of FIG. 1 from which external housing cover has been removed.

FIG. 2 provides further details of the structure of the apparatus, which includes a sample piston and cylinder or syringe assembly, generally designated at 26, a diluent piston and cylinder or syringe assembly, generally designated at 27, and a drive mechanism including a high-resolution stepper motor 28 and guide rods 31 along which a crankplate 32 is slidably mounted. An angle bar 33 is secured to the slidable crankplate 32 to which are secured the respective pistons of the sample piston and cylinder or syringe assembly 26 and of the diluent piston and cylinder or syringe assembly 27 (FIGS. 2 and 3). Each cylinder of the respective piston and cylinder assemblies 26 and 27 is mounted within a stationary top frame plate 34 with the result that the piston and cylinder or syringe assemblies 26 and 27 will operate in response to relative movement of the angle bar 33 of the drive mechanism crankplate 32 with respect to the top frame plate 34.

Diluter apparatus 21 further includes a microprocessor and circuitry assembly 35 that is in operative communication with the key pad 24 and the display 25 in accordance with well-known arrangements. Assembly 35 also functions as a component of a stroke regulating mechanism which, indirectly via stepper motor 28, controls the operation of the sample piston and cylinder assembly 26 and the diluent piston and cylinder assembly 27. The valve actuating mechanism controls operation of a selector valve assembly 36 in timed sequence with operation of the piston and cylinder assemblies 26 and 27. A diluent supply tube 37 provides fluid passing communication between the selector valve assembly 36 and a location external of the apparatus 21. Also included are a power receptacle 38, a power switch 39, and a receptacle 41 for a foot switch or the like.

FIG. 3 provides a more detailed illustration of the structure and operation of the sample piston and cylinder assembly 26 and of the diluent piston and cylinder assembly 27, which are best understood in the context of the general operation of the apparatus 21, such typically proceeding as follows. The diluent supply tube 37 is immersed within a supply of diluent or reagent, and the probe 22 is immersed within the sample to be aspirated and diluted (not shown). At this time, the assembly 35 commands the actuation of gear motor/cam assembly to drive the crankplate 32 downwardly which, in turn, moves the angle bar 33 downwardly to thereby move the respective precision-gound diluent piston 42 and sample piston 45 downwardly within the respective cylinders 43 and 46.

The valve assembly, being positioned by the actuating mechanism, allows communication between the tubing 44 and the diluent supply tube 37 and the diluent piston and cylinder assembly 27, causing a lowering of the pressure within the diluent piston and cylinder assembly 27, by virtue of which the diluent fluid is drawn into the diluent piston and cylinder assembly 27. The downward movement of the sample piston 45 also causes lowering of the pressure within the cylinder 46, the tubing 23 and the probe 22, resulting in aspiration of the fluid sample into the probe 22.

Preferably, the sample piston 45 is structured as previously known so as to include a so-called large cylindrical portion 47 and a so-called small cylindrical portion or top extension 48. The precision-ground diameter of the small cylindrical portion or top extension 48 is slightly less than the precision-ground diameter of the large cylindrical portion 47 such that the sample piston and cylinder assembly 26 is characterized by having a displacement volume defined by an extremely small cross-sectional area, the displacement volume of assembly 26 being the difference between the respective cross-sectional areas of the large cylindrical portion 47 and the small cylindrical portion 48 when taken throughout the length of the stroke.

At the completion of the downward movement of the angle bar 33 and the diluent and sample pistons 42 and 45, and while the cam assembly is in its dwelling period, the valve assembly 36 is actuated by the actuating mechanism, and, in effect, connects the hydraulic passage between the diluent cylinder 43, the selector valve assembly 36, and the sample cylinder 46.

At this stage of the operation of the apparatus 21, a fresh container (not shown) is placed under the probe 22, and assembly 35 commands the actuation of the gear motor/cam assembly to drive the crankplate 32 upwardly, to thereby move the precision-ground diluent piston 42 and sample piston 45 upwardly within their respective cylinders 43 and 46, with the result that the sample is expelled into the fresh container, as is the precisely measured amount of diluent that likewise flows through the probe 22 and into the container so as to provide a diluted sample having an accurate and a precise dilution ratio.

Diluent piston and cylinder assembly 27 further includes a diluent seal assembly, generally designated as 52 and illustrated in enlarged detail in FIGS. 4 and 5. Diluent seal assembly 52 is mounted within an annular slot 53 of the diluent cylinder 43. Diluent seal assembly 52 includes an O-ring 54 mounted within an outer annular groove 55 in a lubricious seal ring 56. Lubricious seal ring 56 includes an internal cylindrical surface 57 having a diameter that is substantially the same as the outer diameter of the diluent piston 42 in order to provide sealing engagement between the diluent seal assembly 52 and the diluent piston 42 that is especially effective and consistent and that does not significantly deteriorate after many thousands of cycles, especially when compared with a seal arrangement wherein an O-ring or the like slidingly engages the movable piston.

Seal assemblies 58 of the sample piston and cylinder assembly 26 are quite similar to the diluent seal assembly 52, each seal assembly 58 also being mounted in an annular slot of the sample piston and cylinder assembly 26. Each sample seal assembly 58 includes an O-ring 59 mounted within an outer annular groove 61 of a lubricious seal ring 62 which has an internal cylindrical sealing surface 63 having a diameter substantially the same as either the large cylindrical portion 47 or the small cylindrical portion 48 of the sample piston 45.

In addition to the high-resolution stepper motor 28, the guide rods 31 and the crankplate 32 having the angle bar 33, the drive mechanism includes other known components (not shown) such as a cam assembly and instrument grade ball bearings. The drive mechanism translates the rotary motion of its shade pole gear motor into reciprocal, linear up and down motion of its crankplate 32 and angle bar 33. The drive mechanism preferably includes structures to achieve progressive increases and decreases in vertical movement and a dwelling period to optimize fluid aspiration, fluid delivery, and timed operation of the selector valve assembly 36. The rigid and precise structure of the drive mechanism contributes no discernible error in crankplate travel and resulting stroke lengths. A lead screw that is driven by the high-resolution stepper motor 28 indirectly regulates piston stroke length in conjunction with the stroke regulating mechanism and its microprocessor and circuitry assembly 35. This high-resolution stroke regulating mechanism enables the resolution of the stroke length to on the order of one part per 1500.

Referring more particularly to the automatic compensation feature of this invention, each of the sample volume and the diluent volume is equal to the net product of cross-sectional fluid-accepting area of syringe 26 or 27 and its piston stroke length. For a syringe 26 or 27 having a stationary seal, the volume of displaced liquid is an integration of cross-sectional areas throughout the stroke length. If the cross-sectional areas for each increment of stroke length were identical through the entire length of piston stroke, the volume of liquid displaced would be the product of area and stroke length. Because of limitations in precision machining techniques, there are finite differences in cross-sectional area for each increment of piston stroke, as a result of which the volumes displaced at differing segments of the piston stroke tend to vary and to deviate from the norm in a random manner. The present invention recognizes this limitation and substantially reduces its detrimental effects in variable volume applications, primarily by increasing or decreasing the number of steps traversed by the stepper motor 28 in order to aspirate or dispense a given volume of fluid in order to compensate for inaccuracies.

For example, a typical stepper motor 28 provides 1500 steps to cover a full piston stroke, with movement to the zero step providing full volume and movement to the 1500 step to providing zero volume. Exemplary compensation in this regard is carried out by programming the microprocessor and circuitry assembly 35 of the stroke regulating mechanism so that the drive mechanism will advance the stepper motor 28 by an increased or decreased number of steps at various locations corresponding to different expected sample or diluent volumes. The extent of increase or decrease is determined during analysis carried out at the time that the apparatus 21 is manufactured or repaired. The number of steps is derived by interpolation from two adjacent measurements, the formula used for computing the number of motor steps needed to achieve the required compensation being as follows:

$$S = \frac{S_2 - S_1}{X_2 - X_1} \cdot |(X - X_1) + S_1|$$

wherein S designates the number of motor steps needed to compensate for these inaccuracies; $S_2$ represents the theoretical, ideal or expected number of steps needed to achieve the closest higher volume; $S_1$ designates the theoretical, ideal or expected number of steps needed to achieve the closest lower volume; $X_2$ is a mean value of measured volumes that were actually experienced by the particular apparatus at the "closest higher volume"; $X_1$ designates the mean of actually measured volumes that correspond to the "closest lower volume"; and X is the expected volume.

In a typical example, a completely perfect and ideal apparatus would require 1380 motor steps to achieve an expected sample volume of 10 μl. However, for illustrative purposes, when 1380 motor steps are performed by the actual apparatus, the volume of liquid that is empirically measured is only 8 μl. After application of the compensation of the type discussed herein including utilization of the preceding formula, it is determined that the number of motor steps with compensation (S) is 1356 steps. When this exemplary apparatus is subsequently utilized, the operator keys in a sample volume of 10, the stroke regulating mechanism determines that, for this particular apparatus, 1356 steps are needed, and the drive mechanism moves the motor 1356 steps so as to aspirate or deliver 10.0 μl of sample. At another volume for this apparatus, the delivery of 100 μl of sample would typically be expected to require 300 motor steps, but when aspirated volumes are measured at 300 steps, the delivered volume is 96.6 μl. After appropriate calculations, it is determined that compensated movement to 259 steps results in the movement of 99.8 μl of liquid, which is significantly more accurate than the uncompensated delivered volume of 96.6 μl.

The compensating diluter/dispenser according to this invention is essentially bias-free and operates in a substantially linear manner throughout its operating range. A typical apparatus 21 according to this invention can be designed to handle sample volumes of between about 5 and 500 μl and diluent volumes of between about 0.25 and 12.5 ml, while experiencing an accuracy of plus or minus 2 standard deviation, which ranges from about 0.2 to 12.0 μl in the volume range of 10 μl to 12.5 ml. When the bias is near the upper limit of the correctable calibration bias, this can be thought of as representing the precision error. Error compensation techniques according to this invention reduce the bias limit to virtually zero. Data illustrating the accuracy and precision attainable by this invention with respect to sample volumes are included in Table I, while those for diluent volumes are shown in Table II. In both of these Tables, X is the run number for each of the ten measurements, $\overline{X}$ designates the mean value, $\sigma$ is the standard deviation, and CV% is the coefficient of variation.

TABLE I

| Sample Volume: | 10 | 20 | 40 | 50 | 100 |
|---|---|---|---|---|---|
| | ul | | | | |
| X: 1 | .0105 mg | .0210 mg | .0411 mg | .0508 mg | .1007 mg |
| 2 | .0103 | .0209 | .0409 | .0509 | .1011 |
| 3 | .0103 | .0209 | .0408 | .0509 | .1008 |
| 4 | .0103 | .0209 | .0410 | .0508 | .1010 |
| 5 | .0104 | .0208 | .0409 | .0510 | .1010 |
| 6 | .0104 | .0208 | .0411 | .0508 | .1010 |
| 7 | .0104 | .0206 | .0409 | .0510 | .1011 |
| 8 | .0104 | .0208 | .0410 | .0509 | .1009 |
| 9 | .0103 | .0208 | .0410 | .0509 | .1009 |
| 10 | .0105 | .0207 | .0409 | .0509 | .1009 |
| $\overline{X}$ | .01038 mg | .02083 mg | .04095 mg | .05088 mg | .10084 mg |
| $\sigma$ | .0001 | .00013 | .0001 | .0001 | .0001 |
| CV % | .76 | .60 | .24 | .16 | .13 |

TABLE II

| Diluent Volume: | .24 | .50 | 1.00 | 1.50 | 2.50 |
|---|---|---|---|---|---|
| | ml | | | | |
| X: 1 | .2492 mg | .5092 mg | 1.0052 mg | 1.5064 mg | 2.5015 mg |
| 2 | .2493 | .5015 | 1.0049 | 1.5061 | 2.5006 |
| 3 | .2493 | .5016 | 1.0050 | 1.5065 | 2.5001 |
| 4 | .2495 | .5018 | 1.0055 | 1.5056 | 2.5007 |
| 5 | .2498 | .5017 | 1.0059 | 1.5059 | 2.5010 |
| 6 | .2496 | .5018 | 1.0061 | 1.5069 | 2.5007 |
| 7 | .2498 | .5019 | 1.0049 | 1.5064 | 2.5011 |
| 8 | .2499 | .5019 | 1.0045 | 1.5065 | 2.4996 |
| 9 | .2493 | .5020 | 1.0046 | 1.5070 | 2.5006 |
| 10 | .2494 | .5022 | 1.0045 | 1.5066 | 2.5015 |
| $\overline{X}$ | .24951 mg | .50182 mg | 1.00511 mg | 1.50639 mg | 2.50072 mg |
| $\sigma$ | .0003 | .0002 | .0006 | .0004 | .0006 |
| CV % | .10 | .04 | .06 | .03 | .02 |

The reported accuracy and precision of a typical precision engineered automatic diluter/dispenser not in accordance with this invention are illustrated in Table III and Table IV as follows:

TABLE III

| 125 ul cylinder Volume ul | Accuracy ± % | Reproducibility % |
|---|---|---|
| 10 | 1.10 | 1.00 |
| 20 | .85 | .75 |
| 40 | .55 | .50 |
| 50 | .30 | .25 |
| 100 | .15 | .12 |

TABLE IV

| 2,500 ul cylinder Volume ul | Accuracy ± % | Reproducibility % |
|---|---|---|
| 250 | .50 | .10 |
| 500 | .40 | .06 |
| 1000 | .30 | .04 |
| 1500 | .15 | .03 |
| 2500 | .10 | .02 |

It will be understood that the embodiments of the present invention which have been described are merely illustrative of a few of the applications of the principles of the present invention. Numerous modifications may be made by those skilled in the art without departing from the true spirit and scope of the invention.

I claim:

1. A compensating precision diluter/dispenser apparatus, comprising:

a piston and cylinder syringe assembly for receiving and dispensing fluids, said piston and cylinder syringe assembly having a plurality of piston positions, each piston position corresponding to an expected volume of fluid to be moved by the piston and cylinder syringe assembly;

a drive assembly for effecting positive displacement of the piston with respect to the cylinder of the syringe assembly;

regulating means for controlling the drive assembly, the regulating means including means for storing piston position and fluid volume data generated during a calibrate mode of the piston and cylinder syringe assembly, the regulating means further including means for varying the stroke length of the piston in view of said piston position and fluid volume data and for thereby compensating for deviations between said expected volume of each said piston position and a delivered volume of fluid that is actually moved by the piston and cylinder assembly at each said piston position of the piston and cylinder syringe assembly, said means for storing data stores data derived from measurements corresponding to a plurality of said delivered volumes, said measurements having been empirically generated during initial calibration of said piston and cylinder syringe assembly, and wherein said regulating means utilizes said stored data to control said stroke-length regulating and compensating means;

selector means for permitting an operator to designate an expected volume to be moved by the piston and cylinder syringe assembly, said selector means being in operative communication with said regulating means; and said regulating means automatically varies the piston stroke length whereby the delivered volume of fluid is substantially identical to the expected volume designated at the selector means substantially throughout said plurality of piston positions.

2. The compensating diluter/dispenser apparatus according to claim 1, further including another said piston and cylinder syringe assembly, wherein one of said piston and cylinder syringe assemblies is for aspirating and dispensing a fluid sample and the other of said piston and cylinder syringe assemblies is for drawing and dispensing a diluent, and wherein a selector valve assembly is in fluid passing communication with both of said piston and cylinder syringe assemblies, said selector valve assembly being indirectly controlled by said regulating means.

3. The compensating diluter/dispenser apparatus according to claim 1, wherein said drive assembly includes a stepper motor and wherein said regulating means automatically selects a number of steps of the stepper motor to achieve said automatic variation of piston stroke length.

4. The compensating diluter/dispenser apparatus according to claim 1, wherein said piston and cylinder syringe assembly includes a seal assembly mounted within an annular slot of said cylinder of the syringe assembly, and said seal assembly includes an O-ring and a lubricious seal ring having a lubricious internal cylindrical surface that slidingly and sealingly engages said piston of the syringe assembly.

5. The precision diluter/dispenser apparatus according to claim 4, wherein said O-ring is mounted within an outer annular groove of said seal ring, and a circumferential surface of said O-ring is in engagement with a radially extending axial surface of said annular slot of the cylinder.

6. The precision diluter/dispenser apparatus according to claim 4, further including another said piston and cylinder syringe assembly, wherein one of said piston and cylinder assemblies is for aspirating and dispensing a fluid sample and the other of said piston and cylinder syringe assemblies is for drawing and dispensing a diluent, wherein a selector valve assembly is in fluid passing communication with both of said piston and cylinder syringe assemblies, and wherein both of said piston and cylinder syringe assemblies includes at least one of said seal assemblies.

7. The precision diluter/dispenser apparatus according to claim 4, wherein said lubricious seal ring of the seal assembly has a generally C-shaped radially directed cross-section.

8. The compensating diluter/dispenser apparatus according to claim 1, wherein said piston and cylinder syringe assembly includes a seal assembly mounted within an annular slot of said cylinder of the syringe assembly, said seal assembly includes an O-ring and a lubricious seal ring having a lubricious internal cylindrical surface that slidingly and sealingly engages said piston of the syringe assembly, and said O-ring is mounted within an outer annular groove of said seal ring, a circumferential surface of said O-ring being in engagement with a radially extending axial surface of said annular slot of the cylinder.

9. A compensating method for a precision diluter/dispenser apparatus of the type including a piston and cylinder syringe assembly having a plurality of piston positions, each piston position corresponding to an expected volume of fluid to be moved by the piston and cylinder syringe assembly, the method comprising:

determining the volume of fluid actually moved by the syringe assembly at a plurality of its piston positions by premeasuring fluid volumes that are actually moved by the syringe assembly at each respective plurality of piston positions during a calibration mode;

comparing each said actual fluid volume with its respective said expected fluid volume;

determining a compensation scheme to correct for the extent of difference between each said respective actual and expected fluid volumes, said determining step including deriving said compensation scheme from said premeasured actual fluid volumes from said respective plurality of piston positions and from said respective fluid volumes;

storing said compensation scheme for regulating piston stroke length during subsequent fluid movement; and said regulating of the piston stroke length automatically varies the piston stroke length whereby the volume of fluid delivered is substantially identical to the respective expected volume substantially throughout said plurality of piston positions.

10. The compensating method according to claim 9, wherein said regulating of the piston stroke length automatically selects a number of steps of a stepper motor for driving the syringe assembly to move the respective expected volume of fluid at each said piston position.

11. The compensating method according to claim 9, further including providing another piston and cylinder syringe assembly and determining and storing another said compensation scheme for regulating piston stroke length thereof;

selectively communicating the respective syringe assemblies; and automatically controlling said selective communicating step and both of said piston stroke length regulating steps to achieve automatic aspiration, dilution and dispensing of a fluid sample volume and of a fluid diluent volume.

* * * * *

UNITED STATES PATENT AND TRADEMARK OFFICE
CERTIFICATE OF CORRECTION

PATENT NO. : 4,702,393

DATED : October 27, 1987

INVENTOR(S) : Chen

It is certified that error appears in the above-identified patent and that said Letters Patent are hereby corrected as shown below: Title page:

In the Abstract, line 5, "with" should read --within--.
Col. 6, line 25, the second factor on the right-hand side of the equation should read $--(X-X_1) + S_1--$ (the brackets should be deleted).

Signed and Sealed this

Twentieth Day of December, 1988

Attest:

DONALD J. QUIGG

Attesting Officer

Commissioner of Patents and Trademarks